(12) United States Patent
Johns et al.

(10) Patent No.: US 9,802,898 B2
(45) Date of Patent: Oct. 31, 2017

(54) PHENYL AND TERTBUTYLACETIC ACID SUBSTITUTED PYRIDINONES HAVING ANTI-HIV EFFECTS

(71) Applicant: VIIV HEALTHCARE UK LIMITED, Brentford, Middlesex (GB)

(72) Inventors: Brian Alvin Johns, Research Triangle Park, NC (US); Emile Johann Velthuisen, Research Triangle Park, NC (US)

(73) Assignee: ViiV HEALTHCARE UK LIMITED, Brentford, Middlesex (GB)

( * ) Notice: Subject to any disclaimer, the term of this patent is extended or adjusted under 35 U.S.C. 154(b) by 0 days.

(21) Appl. No.: 15/326,070

(22) PCT Filed: Jul. 16, 2015

(86) PCT No.: PCT/IB2015/055385
§ 371 (c)(1),
(2) Date: Jan. 13, 2017

(87) PCT Pub. No.: WO2016/012913
PCT Pub. Date: Jan. 28, 2016

(65) Prior Publication Data
US 2017/0217890 A1   Aug. 3, 2017

Related U.S. Application Data

(60) Provisional application No. 62/026,782, filed on Jul. 21, 2014.

(51) Int. Cl.
| | | |
|---|---|---|
| *C07D 213/81* | (2006.01) | |
| *C07D 213/76* | (2006.01) | |
| *C07D 413/04* | (2006.01) | |

(52) U.S. Cl.
CPC ......... *C07D 213/81* (2013.01); *C07D 213/76* (2013.01); *C07D 413/04* (2013.01)

(58) Field of Classification Search
None
See application file for complete search history.

(56) References Cited

FOREIGN PATENT DOCUMENTS

| WO | WO 2005/018557 A2 | 3/2005 |
|---|---|---|
| WO | WO 2007/131350 A1 | 11/2007 |
| WO | WO 2013/002357 A1 | 1/2013 |
| WO | WO 2013/043553 A1 | 3/2013 |
| WO | WO 2014/009794 A1 | 1/2014 |

OTHER PUBLICATIONS

Hyster et al, Chemical Science (2011), 2(8), pp. 1606-1610.*

* cited by examiner

*Primary Examiner* — Zinna Northington Davis
(74) *Attorney, Agent, or Firm* — Robert H. Brink; R. Steve Thomas; Edward R. Gimmi

(57) ABSTRACT

Compounds of Formula I are disclosed and methods of treating viral infections with compositions comprising such compounds.

Formula I

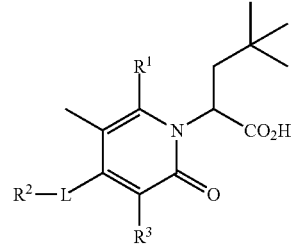

10 Claims, No Drawings

PHENYL AND TERTBUTYLACETIC ACID SUBSTITUTED PYRIDINONES HAVING ANTI-HIV EFFECTS

This application is a §371 of International Application No. PCT/IB2015/055385, filed 16 Jul. 2015, which claims the benefit of U.S. Provisional Application No. 62/026,782, filed 21 Jul. 2014, which are incorporated herein in their entireties.

FIELD OF THE INVENTION

The present invention relates to substituted pyridone compounds, pharmaceutical compositions, and methods of use thereof for (i) inhibiting HIV replication in a subject infected with HIV, or (ii) treating a subject infected with HIV, by administering such compounds.

BACKGROUND OF THE INVENTION

Human immunodeficiency virus type 1 (HIV-1) leads to the contraction of acquired immune deficiency disease (AIDS). The number of cases of HIV continues to rise, and currently over twenty-five million individuals worldwide suffer from the virus. Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still required because of undesirable drug-drug interactions; drug-food interactions; non-adherence to therapy; and drug resistance due to mutation of the enzyme target.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur. The emergence of multidrug-resistant HIV-1 isolates has serious clinical consequences and must be suppressed with a new drug regimen, known as salvage therapy.

Current guidelines recommend that salvage therapy includes at least two, and preferably three, fully active drugs. Typically, first-line therapies combine three to four drugs targeting the viral enzymes reverse transcriptase and protease. One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase inhibitors. However, resistance to all three new drug classes has already been reported both in the lab and in patients. Sustained successful treatment of HIV-1-infected patients with antiretroviral drugs will therefore require the continued development of new and improved drugs with new targets and mechanisms of action.

For example, over the last decade HIV inhibitors have been reported to target the protein-protein interaction between HIV-1 integrase and Lens Epithelium Derived Growth Factor/p75 ("LEDGF"). LEDGF is a cellular transcriptional cofactor of HIV-1 integrase that promotes viral integration of reverse transcribed viral cDNA into the host cell's genome by tethering the preintegration complex to the chromatin. Because of its crucial role in the early steps of HIV replication, the interaction between LEDGF and integrase represents another attractive target for HIV drug therapy.

SUMMARY OF THE INVENTION

Briefly, in one aspect, the present invention discloses compounds of Formula I:

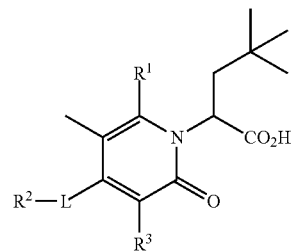

Formula I wherein:
$R^1$ is phenyl optionally substituted by one to four substituents selected from $C_{1-3}$alkyl, halogen, or —$CH_2CH_2CH_2O$— wherein this group is bonded to adjacent carbon atoms on the phenyl to form a ring;

L is a bond, $C_{1-3}$alkylene, —$SO_2$—, —$SO_2CH_2$—, —$NHSO_2$—, —$NHSO_2CH_2$—, —$C(O)$—, —$C(O)NH$—, —$C(O)NHCH_2$—, —$C(O)OCH_2$—, —$C(O)C(O)$—, —$CH_2C(O)$—, $C_{3-7}$heteroaryl, or —$C_{3-7}$heteroarylNH—, wherein each heteroaryl comprises one to three heteroatoms selected from S, N, and O;

$R^2$ is H, cyclohexyl, or phenyl wherein said cyclohexyl and phenyl are optionally substituted by one to three substituents selected from $C_{1-3}$alkyl and halogen $R^3$ is H or —$NHSO_2R^4$ wherein $R^4$ is $C_{1-8}$alkyl and wherein said alkyl can include cycloalkyl portions.

In another aspect the present invention discloses pharmaceutically acceptable salts of the compounds of Formula I.

In another aspect, the present invention discloses pharmaceutical compositions comprising a compound of Formula I or a pharmaceutically acceptable salt thereof.

In another aspect, the present invention discloses a method for treating a viral infection in a patient mediated at least in part by a virus in the retrovirus family of viruses, comprising administering to said patient a composition comprising a compound of Formula I, or a pharmaceutically acceptable salt thereof. In some embodiments, the viral infection is mediated by the HIV virus.

In another aspect, a particular embodiment of the present invention provides a method of treating a subject infected with HIV comprising administering to the subject a therapeutically effective amount of a compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of a compound of Formula I, or a pharmaceutically acceptable salt thereof. Those and other embodiments are further described in the text that follows.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I wherein said virus is an HIV virus and further comprising administration of a therapeutically effective amount of one or more agents active against an HIV virus, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

DETAILED DESCRIPTION OF THE INVENTION

Preferably $R^1$ is phenyl optionally substituted by a methyl group.

Preferably L is a bond, -oxadiazolyl-NH—, —C(O)NH—, or —C(O)NHCH$_2$—.

Preferably $R^2$ is H, cyclohexyl, or phenyl wherein said cyclohexyl and phenyl are optionally substituted by 1 or 2 methyl groups.

Preferably $R^3$ is H, —NHSO$_2$CH$_3$, or —NHSO$_2$CH$_2$cyclohexyl.

Preferably the stereochemistry on the carbon to which the t-butyl group is bound is as depicted below.

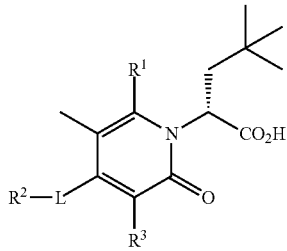

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

EXAMPLES

The compounds of this invention may be made by a variety of methods, including well-known standard synthetic methods. Illustrative general synthetic methods are set out below and then specific compounds of the invention are prepared in the working examples.

Scheme 1

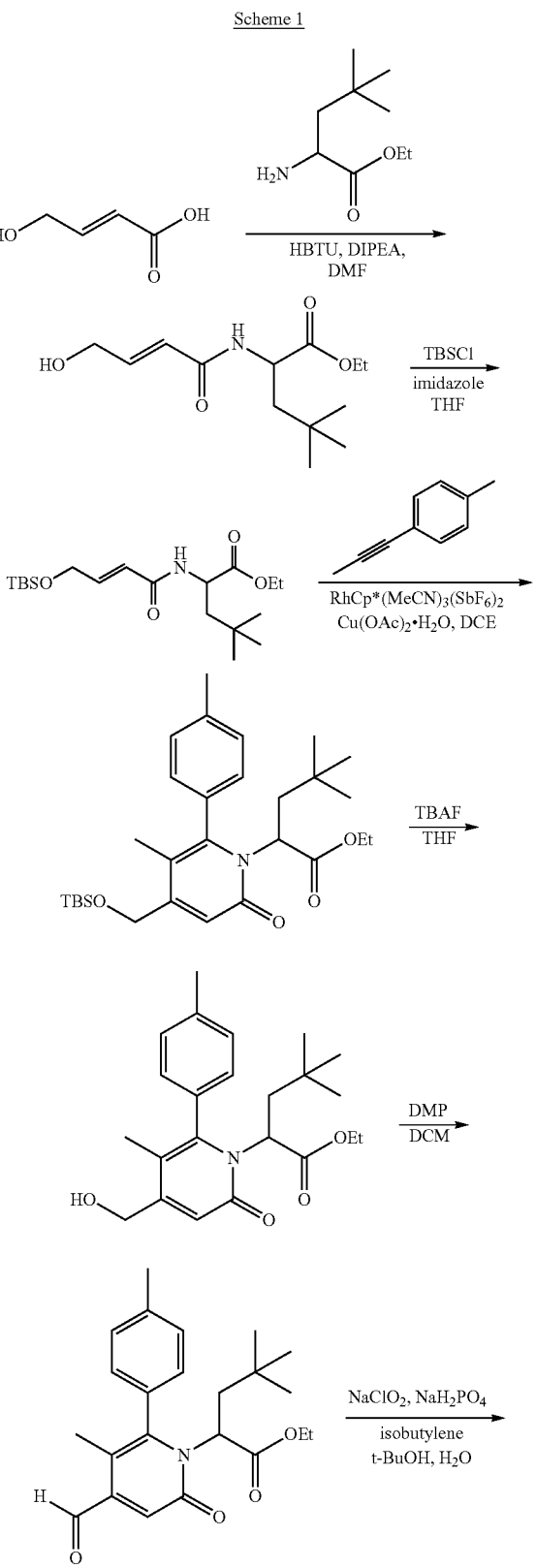

5

-continued

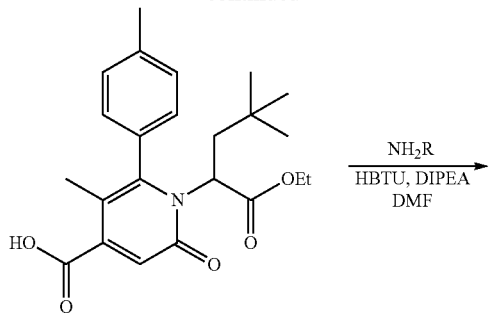

→ NH₂R
HBTU, DIPEA
DMF

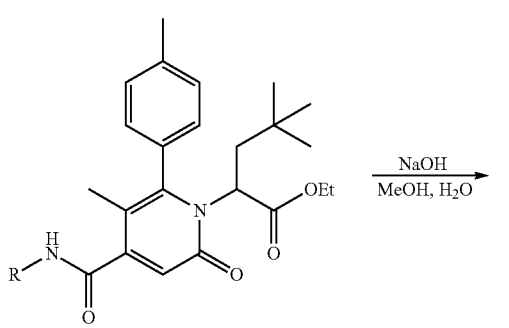

→ NaOH
MeOH, H₂O

Example 1: 4,4-Dimethyl-2-(5-methyl-4-(((1r,4r)-4-methylcyclohexyl)carbamoyl)-2-oxo-6-(p-tolyl)pyridin-1(2H)-yl)pentanoic acid

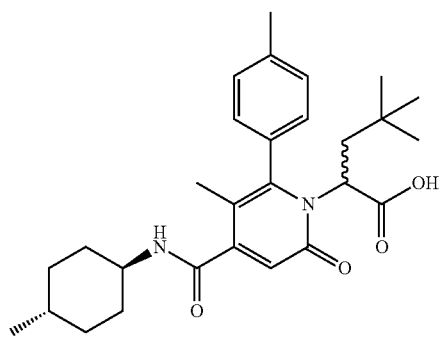 [SMILES: Cc1ccc(-c2c(C)c(C(=O)N[C@H]3CC[C@H](C)CC3)cc(=O)n2C(CC(C)(C)C)C(=O)O)cc1]

6

Step 1: (E)-Ethyl 2-(4-hydroxybut-2-enamido)-4,4-dimethylpentanoate

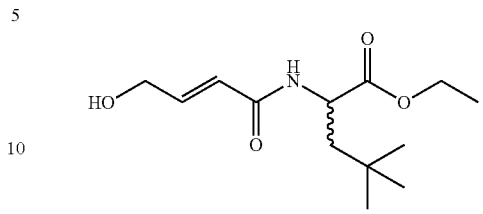

To a solution of (E)-4-hydroxybut-2-enoic acid (418 mg, 4.09 mmol) in DMF (5 mL) were added DIPEA (3.5 mL, 20.5 mmol), HBTU (3.2 g, 8.2 mmol) and ethyl 2-amino-4,4-dimethylpentanoate (1.05 g, 6.1 mmol). After 30 min, the reaction mixture was partitioned between DCM and water. The layers were separated and the aqueous layer was extracted with DCM (20 mL×2). The combined organic layers was washed with NaHCO₃ (aq.) and brine, dried over Na₂SO₄, filtered and concentrated under reduced pressure to give the crude product which was purified by column chromatography (silica gel, PE:EA=1:1) to afford the title compound as a yellow solid (1.05 g, 64% yield). LC-MS (ESI): m/z (M+1)=258.23.

Step 2: (E)-ethyl 2-(4-(tert-butyldimethylsilyloxy)but-2-enamido)-4,4-dimethylpentanoate

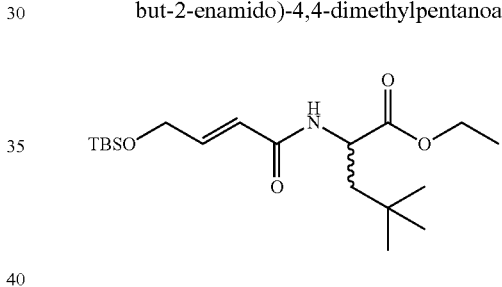

To a solution of (E)-ethyl 2-(4-hydroxybut-2-enamido)-4,4-dimethylpentanoate (1.05 g, 4.1 mmol) in DCM (10 mL) were added DMAP (498 mg, 4.1 mmol), imidazole (833 mg, 12.3 mmol) and TBSCI (922 mg, 6.2 mmol). After 2 h, the reaction mixture was quenched with H₂O and extracted with DCM (20 ml×3). The combined organic layers were washed with brine, dried over Na₂SO₄, filtered and concentrated under reduced pressure to give the crude product which was purified by column chromatography (silica gel, PE:EA=5:1) to afford the title compound as a yellow oil (800 mg, 53% yield). LC-MS (ESI): m/z (M+1)=372.24.

Step 3: Ethyl 2-(4-((tert-butyldimethylsilyloxy)methyl)-5-methyl-2-oxo-6-p-tolylpyridin-1(2H)-yl)-4,4-dimethylpentanoate

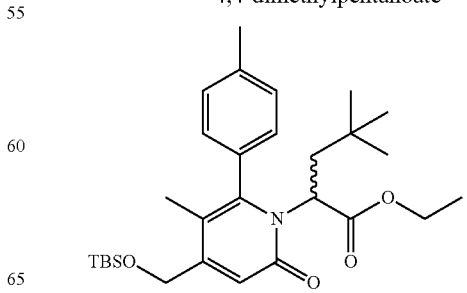

1-Methyl-4-(prop-1-yn-1-yl)benzene was prepared from the known procedure as described in *Angew. Chem. Int. Edit.,* 2012 51, 1287-1294.

A mixture of (E)-ethyl 2-(4-(tert-butyl dimethylsilyloxy) but-2-enamido)-4,4-adimethyl pentanoate (300 mg, 0.81 mmol), 1-methyl-4-(prop-1-ynyl)benzene (132 mg, 1.0 mmol), RhCp*(MeCN)$_3$(SbF$_6$)$_2$ (33.7 mg, 0.04 mmol) and Cu(OAc)$_2$.H$_2$O (340 mg, 1.7 mmol) in DCE (10 mL) was stirred at 80°. After 18 h, the mixture was cooled down to ambient temperature and quenched with 10% NH$_3$.H$_2$O in saturated NH$_4$Cl (aq.) and extracted with DCM (20 mL×3). The combined organic layers was washed with brine, dried over Na$_2$SO$_4$, filtered and concentrated under reduced pressure to give the crude product which was purified by column chromatography (silica gel, 2% MeOH in DCM) to afford the title compound as a yellow solid (114 mg, 28% yield). LC-MS (ESI): m/z (M+1)=500.31

Step 4: Ethyl 2-(4-(hydroxymethyl)-5-methyl-2-oxo-6-p-tolylpyridin-1(2H)-yl)-4,4-dimethylpentanoate

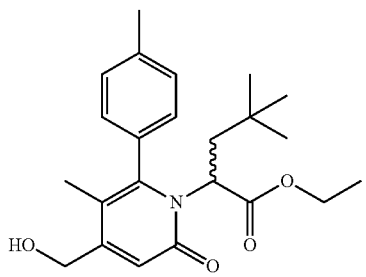 [SMILES: CCOC(=O)C(CC(C)(C)C)n1c(-c2ccc(C)cc2)c(C)c(CO)cc1=O]

To a solution of ethyl 2-(4-((tert-butyldimethylsilyloxy) methyl)-5-methyl-2-oxo-6-p-tolyl pyridin-1(2H)-yl)-4,4-dimethylpentanoate (114 mg, 0.23 mmol) in THF (3 mL) was added TBAF (120 mg, 0.46 mmol). After 1 h, the reaction mixture was partitioned between EtOAc and water. The layers were separated and the organic layer was washed with H2O and brine, dried over Na2SO4, filtered and concentrated under reduced pressure to give the title compound as a yellow oil (108 mg, quant. yield) which was used in next step without further purification. LC-MS (ESI): m/z (M+1) 386.18.

Step 5: Ethyl 2-(4-formyl-5-methyl-2-oxo-6-p-tolylpyridin-1(2H)-yl)-4,4-dimethylpentanoate

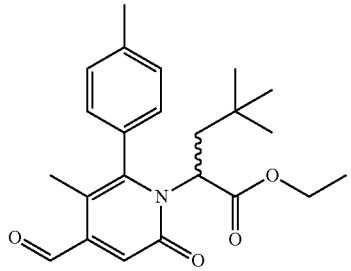 [SMILES: CCOC(=O)C(CC(C)(C)C)n1c(-c2ccc(C)cc2)c(C)c(C=O)cc1=O]

A solution of ethyl 2-(4-(hydroxymethyl)-5-methyl-2-oxo-6-p-tolylpyridin-1(2H)-yl)-4,4-dimethylpentanoate (108 mg, 0.28 mmol) in DCM (5 mL) was added DMP (214 mg, 0.50 mmol). After 1 h, the reaction mixture was quenched with NaHCO$_3$ (aq.) and extracted with DCM (20 ml×3). The combined organic layers was washed with brine, dried over Na$_2$SO$_4$, filtered and concentrated under reduced pressure to give the crude product which was purified by column chromatography (silica gel, PE:EA=2:1) to afford the title compound as a yellow solid (63 mg, 58% yield). LC-MS (ESI): m/z (M+1)=384.3.

Step 6: 1-(1-Ethoxy-4,4-dimethyl-1-oxopentan-2-yl)-5-methyl-2-oxo-6-p-tolyl-1,2-dihydropyridine-4-carboxylic acid

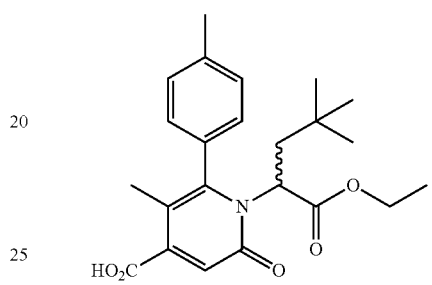

To a solution of ethyl 2-(4-formyl-5-methyl-2-oxo-6-p-tolylpyridin-1(2H)-yl)-4,4-dimethylpentanoate (63 mg, 0.16 mmol) in THF (2.2 mL), t-BuOH (2.2 mL) and isobutylene (4.5 ml) in a sealed tube was added a solution of NaH$_2$PO$_4$ and NaClO$_2$ in H$_2$O (5 mL). After 18 h, the reaction mixture was acidified with 1N HCl (0.5 mL) and extracted with ethyl acetate (20 ml×3). The combined organic layers was washed with brine, dried over Na$_2$SO$_4$, filtered and concentrated under reduced pressure to give the title compound as a yellow solid (51 mg, 80% yield) which was used in next step without further purification. LC-MS (ESI): m/z (M+1)=400.1

Step 7: Ethyl 4,4-dimethyl-2-(5-methyl-4-((1r,4r)-4-methylcyclohexylcarbamoyl)-2-oxo-6-p-tolylpyridin-1(2H)-yl)pentanoate

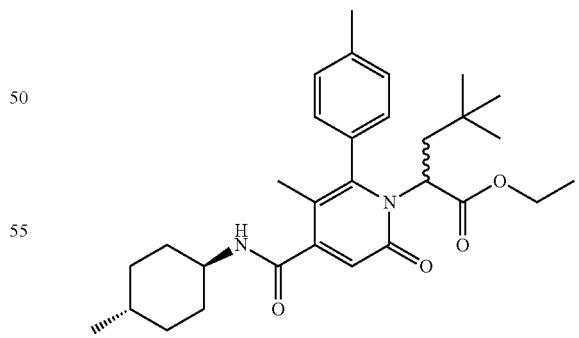

A solution of 1-(1-ethoxy-4,4-dimethyl-1-oxopentan-2-yl)-5-methyl-2-oxo-6-p-tolyl-1,2-dihydropyridine-4-carboxylic acid (28 mg, 0.07 mmol) in DMF (2 mL) was treated with DIPEA (0.06 ml, 0.35 mmol), HBTU (54.2 mg, 0.14 mmol) and trans-4-methyl cyclohexyl amine (0.02 ml, 0.14 mmol). After 18 h, the reaction mixture was diluted with water and extracted with DCM (20 ml×3). The combined organic layers was washed with NaHCO₃ (aq.) and brine, dried over Na₂SO₄, filtered and concentrated under reduced pressure to give the crude product which was purified by prep. TLC (PE:EA=1:1) to afford the title compound as a yellow solid (30 mg, 86%). LC-MS (ESI): m/z (M+1)=495.37.

Step 8: 4,4-Dimethyl-2-(5-methyl-4-((1r,4r)-4-methylcyclohexylcarbamoyl)-2-oxo-6-p-tolylpyridin-1(2H)-yl)pentanoic acid

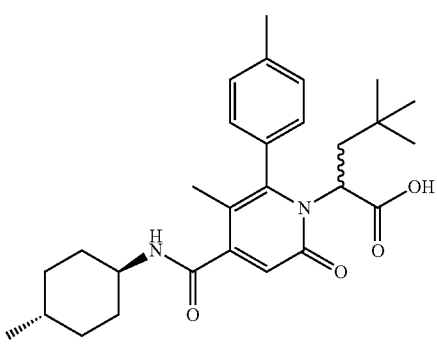 [SMILES: Cc1ccc(-c2c(C)c(C(=O)N[C@H]3CC[C@H](C)CC3)cc(=O)n2C(CC(C)(C)C)C(=O)O)cc1]

To a solution of ethyl 4,4-dimethyl-2-(5-methyl-4-((1r,4r)-4-methylcyclohexylcarbamoyl)-2-oxo-6-p-tolylpyridin-1(2H)-yl)pentanoate (30 mg, 0.06 mmol) in MeOH (2 mL) was added 1 N NaOH (0.6 mL) and heated to reflux. After 18 h, the reaction mixture was cooled to ambient temperature, acidified with 1 N HCl (0.6 mL) (pH=6~7) and concentrated under reduced pressure to give the crude product which was purified by reverse phase HPLC (C₁₈ 70~100% CH₃CN in H₂O with 0.1% formic acid) to afford the title compound as a white powder (12 mg, 40% yield). ¹H NMR (400 MHz, DMSO) δ 8.43 (d, J=8.0 Hz, 1H), 7.46-7.31 (m, 3H), 7.28 (d, J=8.1 Hz, 1H), 6.24 (s, 1H), 4.19 (s, 1H), 3.63-3.58 (m, 1H), 2.39 (s, 3H), 2.31-2.23 (m, 1H), 1.92-1.77 (m, 3H), 1.76-1.60 (m, 5H), 1.32-1.23 (m, 3H), 1.05-0.95 (m, 2H), 0.87 (d, J=6.5 Hz, 3H), 0.58 (s, 9H). LC-MS (ESI): m/z (M+1)=467.33.

Scheme 2

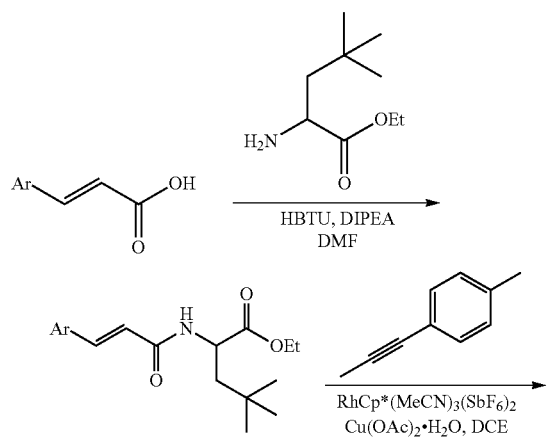

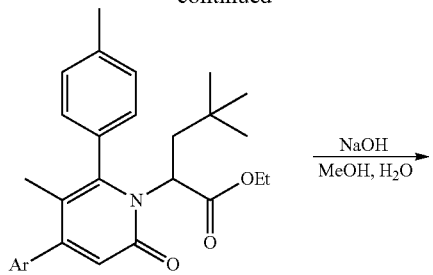

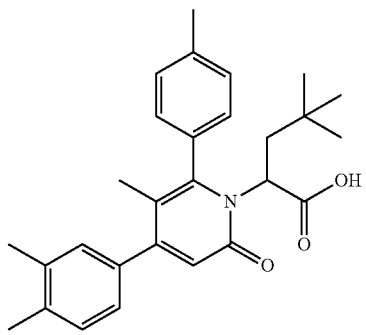 [SMILES: Cc1ccc(-c2c(C)c(-c3ccc(C)c(C)c3)cc(=O)n2C(CC(C)(C)C)C(=O)O)cc1]

Example 2: 2-(4-(3,4-Dimethylphenyl)-5-methyl-2-oxo-6-(p-tolyl)pyridin-1(2H)-yl)-4,4-dimethylpentanoic acid Step 1: (E)-Ethyl 2-(3-(3,4-dimethylphenyl)acrylamido)-4,4-dimethylpentanoate

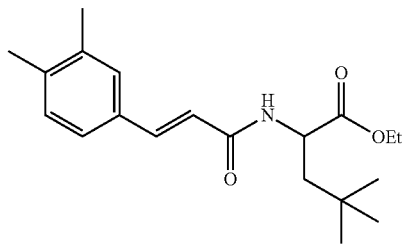 [SMILES: CCOC(=O)C(CC(C)(C)C)NC(=O)/C=C/c1ccc(C)c(C)c1]

A mixture of (E)-3-(3,4-dimethylphenyl)acrylic acid (200 mg, 1.14 mmol), ethyl 2-amino-4,4-dimethylpentanoate (240 mg, 1.4 mmol), HBTU (880 mg, 2.3 mmol) and DIPEA (733 mg, 5.7 mmol) in DCM (10 mL) was stirred at r.t. for 40 min. The reaction mixture was diluted with sat. NaHCO₃ (aq.) and extracted with DCM (20 ml×3). The combined organic layers were washed with brine, dried over Na₂SO₄, filtered and concentrated under reduced pressure to give the crude product which was purified by column chromatography (silica gel, PE:EA=3:1) to afford the title compound as a yellow oil (288 mg, 77% yield). LC-MS (ESI): m/z (M+1)=332.3.

Step 2: Ethyl 2-(4-(3,4-dimethylphenyl)-5-methyl-2-oxo-6-(p-tolyl)pyridin-1(2H)-yl)-4,4-dimethylpentanoate

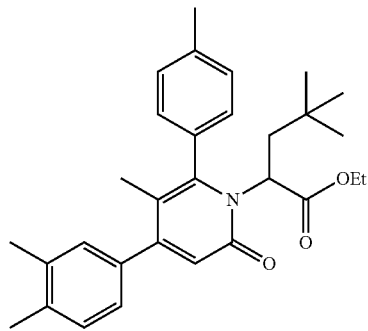 [SMILES: CCOC(=O)C(CC(C)(C)C)n1c(-c2ccc(C)cc2)c(C)c(-c2ccc(C)c(C)c2)cc1=O]

A mixture of (E)-Ethyl 2-(3-(3,4-dimethylphenyl)acrylamido)-4,4-dimethylpentanoate (60 mg, 0.18 mmol), 1-methyl-4-(prop-1-ynyl)benzene (24 mg, 0.18 mmol), RhCp*(MeCN)$_3$(SbF$_6$)$_2$ (7.5 mg, 0.01 mmol) and Cu(OAc)$_2$.H$_2$O (152 mg, 0.76 mmol) in DCE (2 mL) was stirred at 100° C. After 24 h, the mixture was cooled down to ambient temperature and quenched with 10% NH$_3$.H$_2$O in saturated NH$_4$Cl (aq.) and extracted with DCM (10 mL×3). The combined organic layers was washed with brine, dried over Na$_2$SO$_4$, filtered and concentrated under reduced pressure to give the crude product which was purified by column chromatography (silica gel, PE:EA=3:1) to afford the title compound as a yellow oil (50 mg, 60% yield). LC-MS (ESI): m/z (M+1)=460.5.

Step 3: 2-(4-(3,4-dimethylphenyl)-5-methyl-2-oxo-6-(p-tolyl)pyridin-1(2H)-yl)-4,4-dimethylpentanoic acid

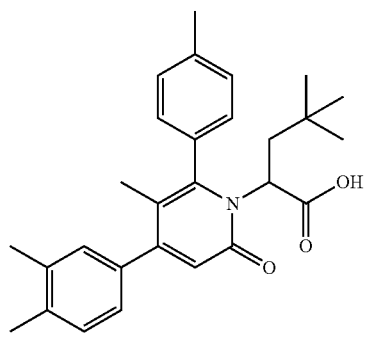 [SMILES: Cc1ccc(-c2c(C)c(-c3ccc(C)c(C)c3)cc(=O)n2C(CC(C)(C)C)C(=O)O)cc1]

To a solution of Ethyl 2-(4-(3,4-dimethylphenyl)-5-methyl-2-oxo-6-(p-tolyl)pyridin-1(2H)-yl)-4,4-dimethylpentanoate (50 mg, 0.11 mmol) in MeOH (2 mL) was added 1 N NaOH (1.0 mL) and heated to reflux. After 12 h, the reaction mixture was cooled to ambient temperature, acidified with 1 N HCl (1.0 mL) (pH=6~7) and concentrated under reduced pressure to give the crude product which was purified by reverse phase HPLC (C$_{18}$ 50~100% CH$_3$CN in H$_2$O with 0.1% formic acid) to afford the title compound as a white powder (37 mg, 77% yield). $^1$H NMR (400 MHz, DMSO) δ 12.86 (br, 1H), 7.57-6.99 (m, 7H), 6.24 (s, 1H), 4.27 (s, 1H), 2.39 (s, 3H), 2.36-2.15 (m, 7H), 1.96-1.79 (m, 1H), 1.58 (s, 3H), 0.61 (s, 9H). LC-MS (ESI): m/z (M+1)=432.4.

Scheme 3

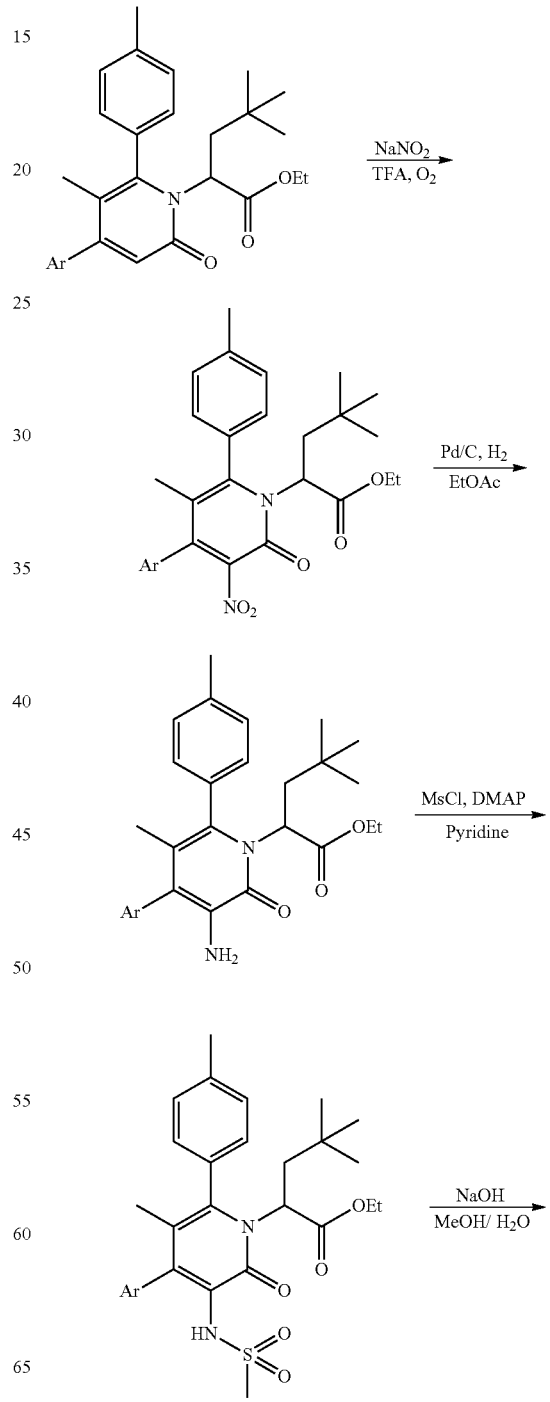

-continued

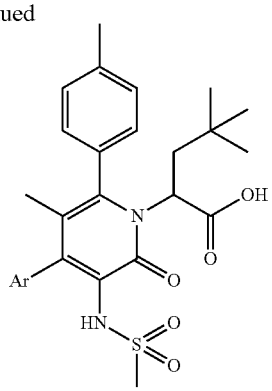

Example 3: 2-(4-(3,4-dimethylphenyl)-5-methyl-3-(methylsulfonamido)-2-oxo-6-(p-tolyl)pyridin-1(2H)-yl)-4,4-dimethylpentanoic acid

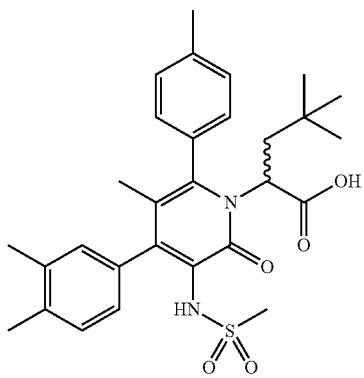 [SMILES: Cc1ccc(-c2c(C)c(-c3ccc(C)c(C)c3)c(NS(C)(=O)=O)c(=O)n2C(CC(C)(C)C)C(=O)O)cc1]

Step 1: Ethyl 2-(4-(3,4-dimethylphenyl)-5-methyl-3-nitro-2-oxo-6-(p-tolyl)pyridin-1(2H)-yl)-4,4-dimethylpentanoate

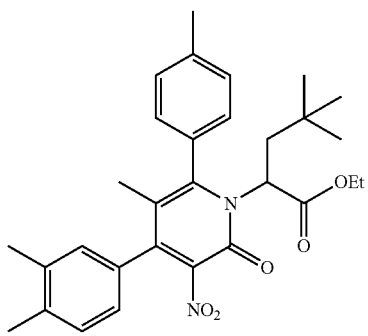 [SMILES: CCOC(=O)C(CC(C)(C)C)n1c(-c2ccc(C)cc2)c(C)c(-c2ccc(C)c(C)c2)c([N+](=O)[O-])c1=O]

To a mixture of Ethyl 2-(4-(3,4-dimethylphenyl)-5-methyl-2-oxo-6-p-tolylpyridin-1(2H)-yl)-4,4-dimethylpentanoate (153 mg, 0.33 mmol) and NaNO$_2$ (28 mg, 0.37 mmol) in DCM (5 mL) was added TFA (0.5 mL) under O$_2$ atmosphere. After 12 h, the reaction mixture was quenched with sat. NaHCO$_3$ (aq.) and extracted with DCM (20 ml×3). The combined organic layers were washed with brine, dried over Na$_2$SO$_4$, filtered and concentrated under reduced pres- sure to give the crude product which was purified by column chromatography (silica gel, PE:EA=3:1) to afford the title compound as a yellow oil (140 mg, 83% yield). LC-MS (ESI): m/z (M+1)=505.3.

Step 2: Ethyl 2-(3-amino-4-(3,4-dimethylphenyl)-5-methyl-2-oxo-6-(p-tolyl)pyridin-1(2H)-yl)-4,4-dimethylpentanoate

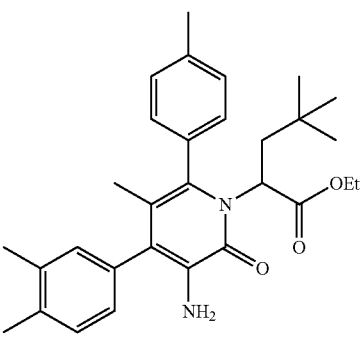 [SMILES: CCOC(=O)C(CC(C)(C)C)n1c(-c2ccc(C)cc2)c(C)c(-c2ccc(C)c(C)c2)c(N)c1=O]

A mixture of Ethyl 2-(4-(3,4-dimethylphenyl)-5-methyl-3-nitro-2-oxo-6-p-tolylpyridin-1(2H)-yl)-4,4-dimethylpentanoate (140 mg, 0.28 mmol) and Pd/C (130 mg) in EtOAc (5 mL) was purged with H$_2$ three times. After 2 h, the reaction mixture was filtered through Celite pad and the filtrate was concentrated under reduced pressure to afford the title compound as a yellow solid (133 mg, 99% yield). LC-MS (ESI): m/z (M+1)=475.4.

Step 3: Ethyl 2-(4-(3,4-dimethylphenyl)-5-methyl-3-(methylsulfonamido)-2-oxo-6-(p-tolyl)pyridin-1(2H)-yl)-4,4-dimethylpentanoate

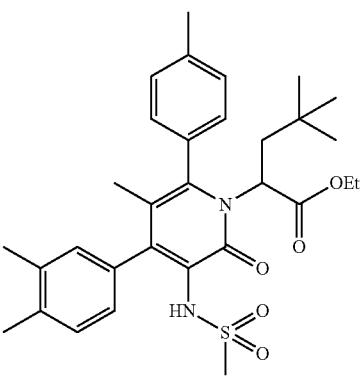 [SMILES: CCOC(=O)C(CC(C)(C)C)n1c(-c2ccc(C)cc2)c(C)c(-c2ccc(C)c(C)c2)c(NS(C)(=O)=O)c1=O]

To a solution of Ethyl 2-(4-(3,4-dimethylphenyl)-5-methyl-3-(methylsulfonamido)-2-oxo-6-(p-tolyl)pyridin-1(2H)-yl)-4,4-dimethylpentanoate (36 mg, 0.076 mmol) and DMAP (5 mg, 0.003 mmol) in pyridine (1 mL) was added MsCl (44 mg, 0.38 mmol). After 12 h, the reaction mixture was diluted with sat. NH$_4$Cl (aq.) and extracted with EtOAc (10 ml×3). The combined organic layers were washed with brine, dried over Na$_2$SO$_4$, filtered and concentrated under reduced pressure to give the crude product which was purified by column chromatography (silica gel, PE:EA=2:1) to afford the title compound as a yellow oil (24 mg, 57% yield). LC-MS (ESI): m/z (M+1)=553.4.

Step 4: 2-(4-(3,4-Dimethylphenyl)-5-methyl-3-(methylsulfonamido)-2-oxo-6-(p-tolyl)pyridin-1(2H)-yl)-4,4-dimethylpentanoic acid

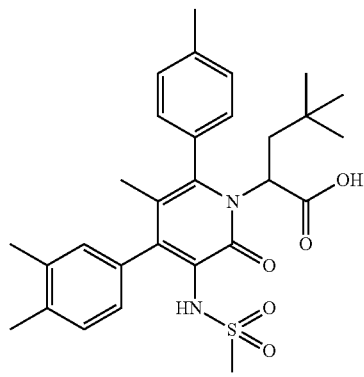 [SMILES: Cc1ccc(-c2c(C)c(-c3ccc(C)c(C)c3)c(NS(C)(=O)=O)c(=O)n2C(CC(C)(C)C)C(=O)O)cc1]

To a solution of Ethyl 2-(4-(3,4-dimethylphenyl)-5-methyl-3-(methylsulfonamido)-2-oxo-6-(p-tolyl)pyridin-1(2H)-yl)-4,4-dimethylpentanoate (30 mg, 0.054 mmol) in MeOH (2 mL) was added 1 N NaOH (0.6 mL) and heated to reflux. After 12 h, the reaction mixture was cooled to ambient temperature, acidified with 1 N HCl (0.6 mL) (pH=6~7) and concentrated under reduced pressure to give the crude product which was purified by reverse phase HPLC ($C_{18}$ 60~100% $CH_3CN$ in $H_2O$ with 0.1% formic acid) to afford the title compound as a white powder (14 mg, 49% yield). $^1$H NMR (400 MHz, DMSO) δ 12.93 (br, 1H), 8.30 (s, 1H), 7.51-7.27 (m, 4H), 7.28-7.16 (m, H), 7.08-6.92 (m, 2H), 4.31 (s, 1H), 2.91 (d, J=4.6 Hz, 3H), 2.41-2.31 (m, 4H), 2.31-2.18 (m, 6H), 1.94-1.86 (m, 1H), 1.41 (s, 3H), 0.61 (s, 9H). LC-MS (ESI): m/z (M+1)=525.8.

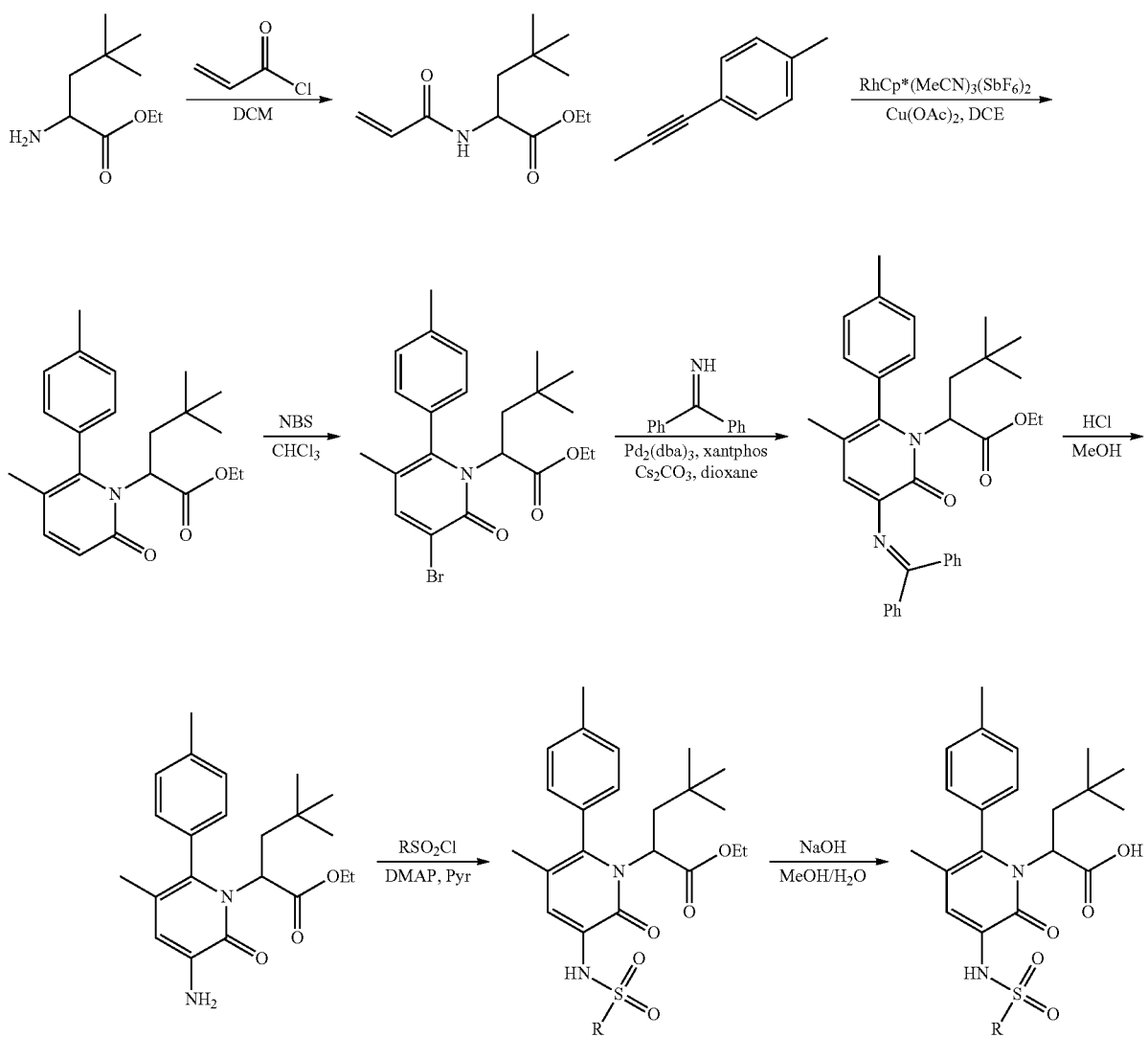

Scheme 4

Example 4: 4,4-Dimethyl-2-(5-methyl-3-(methylsulfonamido)-2-oxo-6-(p-tolyl)pyridin-1(2H)-yl)pentanoic acid

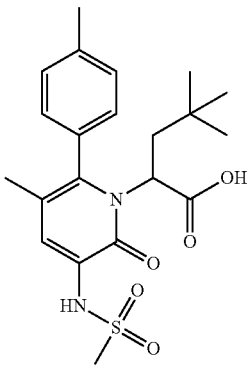 [SMILES: Cc1ccc(-c2c(C)cc(NS(C)(=O)=O)c(=O)n2C(CC(C)(C)C)C(=O)O)cc1]

Step 1: Ethyl 2-acrylamido-4,4-dimethylpentanoate

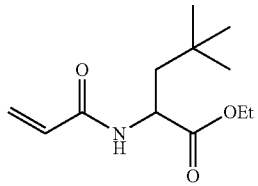 [SMILES: C=CC(=O)NC(CC(C)(C)C)C(=O)OCC]

To a solution of Ethyl 2-amino-4,4-dimethylpentanoate (150 mg, 0.86 mmol) in DCM (4 mL) was added acryloyl chloride (156 mg, 1.72 mmol). After 1 h, the reaction mixture was diluted with sat. NaHCO$_3$ (aq.) and extracted with DCM (20 ml×2). The combined organic layers were washed with brine, dried over Na$_2$SO$_4$, filtered and concentrated under reduced pressure to give the crude product which was purified by column chromatography (silica gel, DCM:MeOH=20:1) to afford the title compound as a yellow solid (190 mg, 96% yield). LC-MS (ESI): m/z (M+1)=228.3.

Step 2: Ethyl 4,4-dimethyl-2-(5-methyl-2-oxo-6-(p-tolyl)pyridin-1(2H)-yl)pentanoate

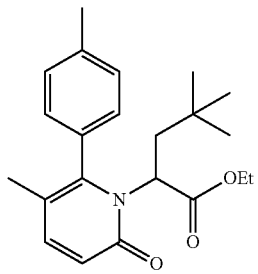 [SMILES: CCOC(=O)C(CC(C)(C)C)n1c(-c2ccc(C)cc2)c(C)ccc1=O]

A mixture of Ethyl 2-acrylamido-4,4-dimethylpentanoate (200 mg, 0.18 mmol), 1-methyl-4-(prop-1-ynyl)benzene (250 mg, 0.35 mmol), RhCp*(MeCN)$_3$(SbF$_6$)$_2$ (30 mg, 0.01 mmol) and Cu(OAc)$_2$.H$_2$O (365 mg, 0.37 mmol) in DCE (4 mL) was stirred at 100° C. After 24 h, the mixture was cooled down to ambient temperature and quenched with 10% NH$_3$.H$_2$O in saturated NH$_4$Cl (aq.) and extracted with DCM (10 mL×3). The combined organic layers was washed with brine, dried over Na$_2$SO$_4$, filtered and concentrated under reduced pressure to give the crude product which was purified by column chromatography (silica gel, PE:EA=2:1) to afford the title compound as a yellow oil (50 mg, 16% yield). LC-MS (ESI): m/z (M+1)=356.2.

Step 3: Ethyl 2-(3-bromo-5-methyl-2-oxo-6-(p-tolyl)pyridin-1(2H)-yl)-4,4-dimethylpentanoate

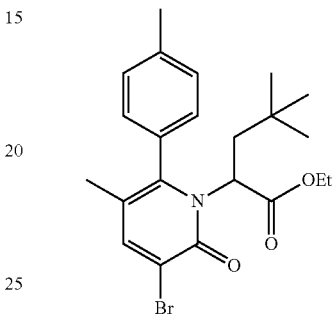

To a solution of Ethyl 4,4-dimethyl-2-(5-methyl-2-oxo-6-(p-tolyl)pyridin-1(2H)-yl)pentanoate (105 mg, 0.3 mmol) in CHCl$_3$ (4 mL) was added NBS (61 mg, 0.33 mmol) and heated to 40° C. After 12 h, the reaction mixture was diluted with water and extracted with DCM (20 ml×2). The combined organic layers were washed with brine, dried over Na$_2$SO$_4$, filtered and concentrated under reduced pressure to give the crude product which was purified by column chromatography (silica gel, PE:EA=5:1) to afford the title compound as a yellow oil (115 mg, 90% yield). LC-MS (ESI): m/z (M/M+2)=434.2/436.2.

Step 4: Ethyl 2-(3-((diphenylmethylene)amino)-5-methyl-2-oxo-6-(p-tolyl)pyridin-1(2H)-yl)-4,4-dimethylpentanoate

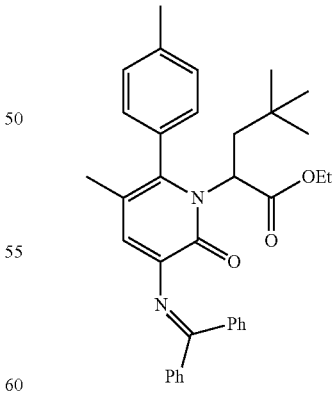

A mixture of Ethyl 2-(3-bromo-5-methyl-2-oxo-6-(p-tolyl)pyridin-1(2H)-yl)-4,4-dimethylpentanoate (130 mg, 0.30 mmol), diphenylmethanimine (165 mg, 0.90 mmol), Pd$_2$(dba)$_3$ (30 mg, 0.03 mmol), Xantphos (17 mg, 0.03 mmol) and Cs$_2$CO$_3$ (292 mg, 0.90 mmol) in dioxane (3 mL) was stirred at 90° C. under N$_2$ atmosphere. After 20 h, the mixture was cooled down to ambient temperature, diluted with water and extracted with EtOAc (20 mL×3). The combined organic layers was washed with brine, dried over Na₂SO₄, filtered and concentrated under reduced pressure to give the crude product which was purified by column chromatography (silica gel, PE:EA=3:1) to afford the title compound as a yellow oil (100 mg, 63% yield). LC-MS (ESI): m/z (M+1)=535.3.

Step 5: Ethyl 2-(3-amino-5-methyl-2-oxo-6-(p-tolyl) pyridin-1(2H)-yl)-4,4-dimethylpentanoate

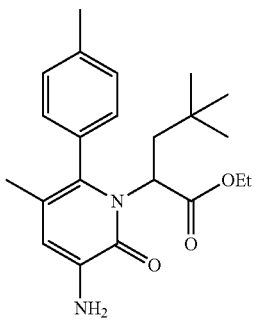 [SMILES: CCOC(=O)C(CC(C)(C)C)n1c(-c2ccc(C)cc2)c(C)cc(N)c1=O]

To a solution of Ethyl 2-(3-((diphenylmethylene)amino)-5-methyl-2-oxo-6-(p-tolyl)pyridin-1(2H)-yl)-4,4-dimethyl-pentanoate (100 mg, 0.19 mmol) in MeOH (5 mL) was added 1 N HCl (1 mL). After 1 h, the reaction mixture was neutralized with sat. NaHCO₃ (aq.) and extracted with DCM (20 ml×2). The combined organic layers were washed with brine, dried over Na₂SO₄, filtered and concentrated under reduced pressure to give the crude product which was purified by column chromatography (silica gel, PE:EA=2:1) to afford the title compound as a yellow oil (53 mg, 77% yield). ¹H NMR (400 MHz, DMSO) δ 7.31 (t, J=6.9 Hz, 2H), 7.23 (dd, J=8.7, 7.1 Hz, 2H), 6.40 (s, 1H), 5.13 (s, 2H), 4.32 (s, 1H), 4.22-4.11 (m, 1H), 4.10-3.95 (m, 2H), 2.36 (s, 3H), 2.28-2.19 (m, 1H), 1.89-1.79 (m, 1H), 1.74 (s, 3H), 1.17 (q, J=7.1 Hz, 3H), 0.56 (s, 9H). LC-MS (ESI): m/z (M+1)=371.2.

Step 6: Ethyl 4,4-dimethyl-2-(5-methyl-3-(methyl-sulfonamido)-2-oxo-6-(p-tolyl)pyridin-1(2H)-yl) pentanoate

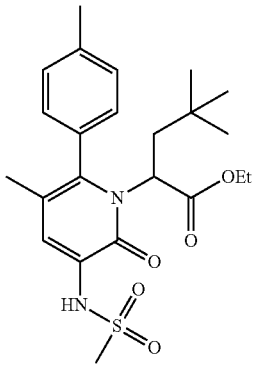 [SMILES: CCOC(=O)C(CC(C)(C)C)n1c(-c2ccc(C)cc2)c(C)cc(NS(C)(=O)=O)c1=O]

To a solution of Ethyl 2-(3-amino-5-methyl-2-oxo-6-(p-tolyl)pyridin-1(2H)-yl)-4,4-dimethylpentanoate (13 mg, 0.035 mmol) and DMAP (1 mg, 0.008 mmol) in pyridine (2 mL) was added MsCl (12 mg, 0.105 mmol). After 1 h, the reaction mixture was quenched with sat. NH₄Cl (aq.) and extracted with DCM (20 ml×2). The combined organic layers were washed with brine, dried over Na₂SO₄, filtered and concentrated under reduced pressure to afford the title compound as a yellow oil (53 mg, 77% yield) which was used in next step without further purification. LC-MS (ESI): m/z (M+1)=449.3.

Step 7: 4,4-Dimethyl-2-(5-methyl-3-(methylsulfona-mido)-2-oxo-6-(p-tolyl)pyridin-1(2H)-yl)pentanoic acid

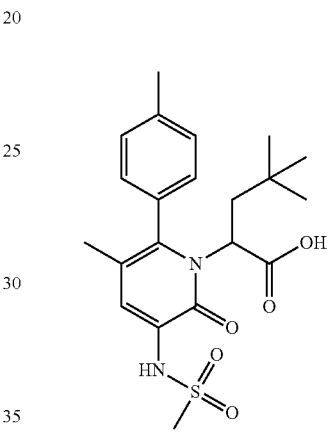

To a solution of Ethyl 4,4-dimethyl-2-(5-methyl-3-(methylsulfonamido)-2-oxo-6-(p-tolyl)pyridin-1(2H)-yl)pentanoate (15 mg, 0.033 mmol) in MeOH (3 mL) was added 1 N NaOH (0.3 mL) and heated to reflux. After 6 h, the reaction mixture was cooled to ambient temperature, acidified with 1 N HCl (0.3 mL) (pH=6~7) and concentrated under reduced pressure to give the crude product which was purified by reverse phase HPLC (C₁₈ 60~100% CH₃CN in H₂O with 0.1% formic acid) to afford the title compound as a white powder (7 mg, 50% yield). ¹H NMR (400 MHz, DMSO) δ 12.93 (br, 1H), 8.88 (s, 1H), 7.45-7.22 (m, 5H), 4.34 (s, 1H), 3.09 (s, 3H), 2.39 (s, 3H), 2.23 (dd, J=15.1, 3.7 Hz, 1H), 1.98-1.91 (m, 1H), 1.81 (s, 3H), 0.57 (s, 9H). LC-MS (ESI): m/z (M+1)=421.2.

Scheme 5

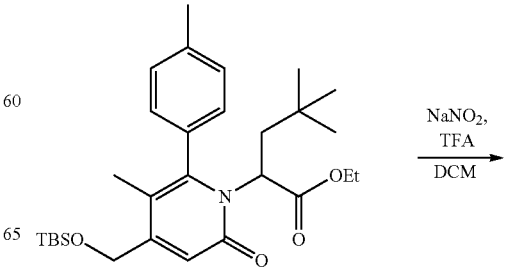

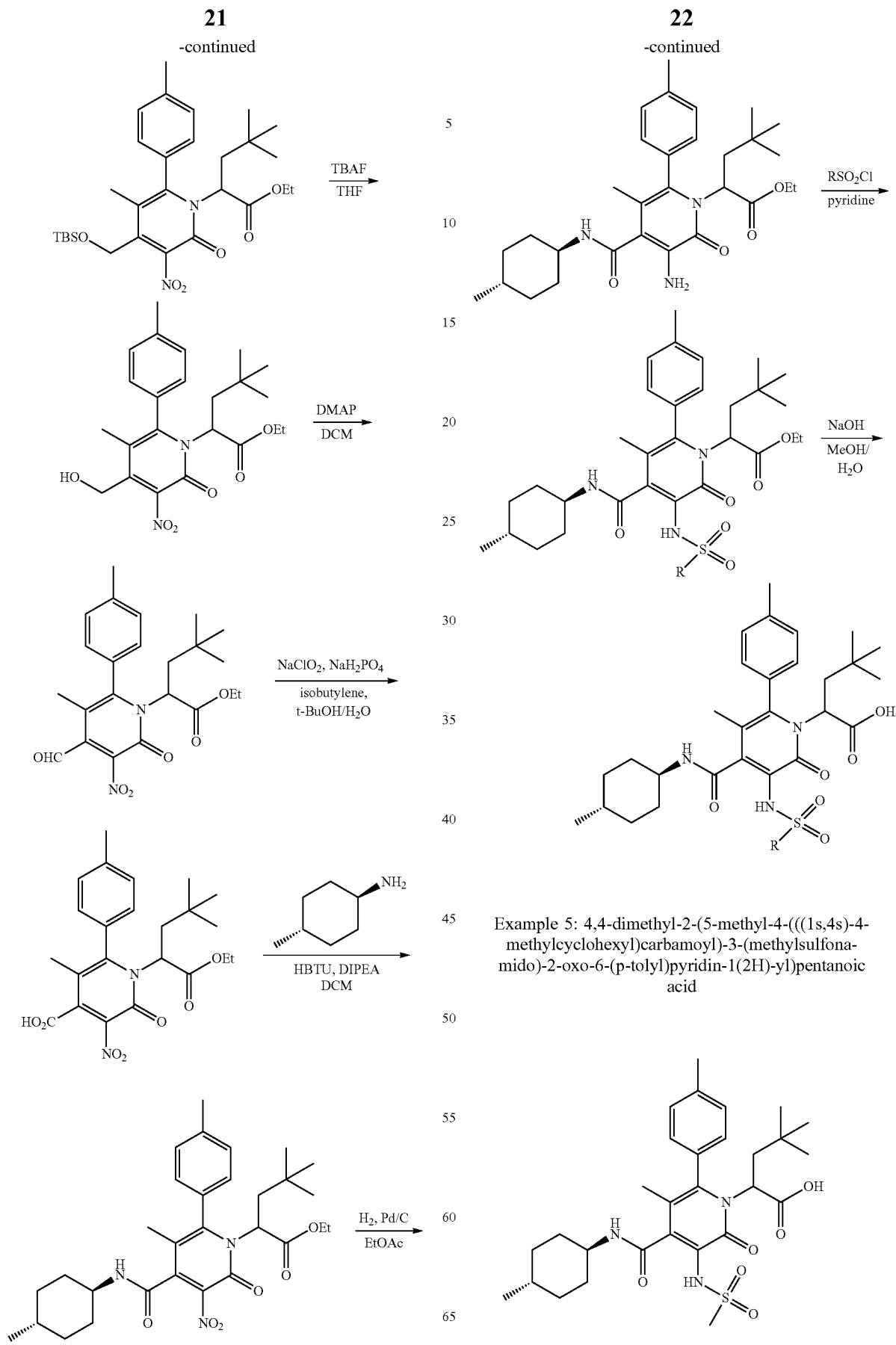
Example 5: 4,4-dimethyl-2-(5-methyl-4-(((1s,4s)-4-methylcyclohexyl)carbamoyl)-3-(methylsulfonamido)-2-oxo-6-(p-tolyl)pyridin-1(2H)-yl)pentanoic acid

Step 1: Ethyl 2-(4-(((tert-butyldimethylsilyl)oxy) methyl)-5-methyl-3-nitro-2-oxo-6-(p-tolyl)pyridin-1 (2H)-yl)-4,4-dimethylpentanoate

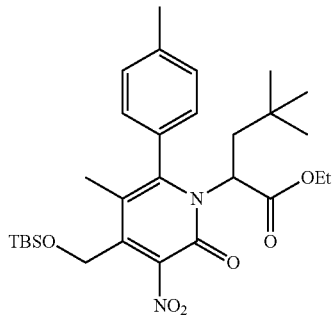 [SMILES: CCOC(=O)C(CC(C)(C)C)n1c(-c2ccc(C)cc2)c(C)c(CO[Si](C)(C)C(C)(C)C)c([N+](=O)[O-])c1=O]

To a mixture of Ethyl 2-(4-((tert-butyldimethylsilyloxy) methyl)-5-methyl-2-oxo-6-p-tolylpyridin-1(2H)-yl)-4,4-dimethylpentanoate (50 mg, 0.10 mmol), NaNO$_2$ (7.5 mg, 0.11 mmol) in DCM (5 mL) was added TFA (0.05 mL) under O$_2$ atmosphere. After 12 h, the reaction mixture was quenched with sat. NaHCO$_3$ (aq.) and extracted with DCM (20 mL×3). The combined organic layers were washed with brine, dried over Na$_2$SO$_4$, filtered and concentrated under reduced pressure to give the crude product which was purified by column chromatography (silica gel, PE:EA=5:1) to afford the title compound as a yellow oil (54 mg, 92% yield). LC-MS (ESI): m/z (M+1)=545.6.

Step 2: Ethyl 2-(4-(hydroxymethyl)-5-methyl-3-nitro-2-oxo-6-(p-tolyl)pyridin-1(2H)-yl)-4,4-dimethylpentanoate

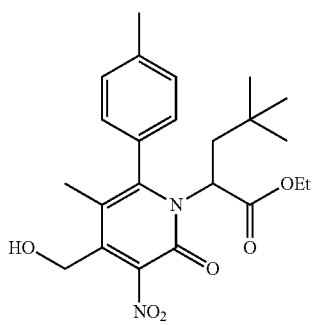 [SMILES: CCOC(=O)C(CC(C)(C)C)n1c(-c2ccc(C)cc2)c(C)c(CO)c([N+](=O)[O-])c1=O]

To a solution of Ethyl 2-(4-(((tert-butyldimethylsilyl)oxy) methyl)-5-methyl-3-nitro-2-oxo-6-(p-tolyl)pyridin-1(2H)-yl)-4,4-dimethylpentanoate (138 mg, 0.25 mmol) in THF (10 mL) was added TBAF (133 mg, 0.51 mmol). After 30 min, the reaction mixture was partitioned between EtOAc and water. The layers were separated and the organic layer was washed with H$_2$O and brine, dried over Na$_2$SO$_4$, filtered and concentrated under reduced pressure to give the crude product which was purified by column chromatography (silica gel, PE:EA=2:1) to afford the title compound as a yellow oil (104 mg, 95% yield). LC-MS (ESI): m/z (M+1) 431.4.

Step 3: Ethyl 2-(4-formyl-5-methyl-3-nitro-2-oxo-6-(p-tolyl)pyridin-1(2H)-yl)-4,4-dimethylpentanoate

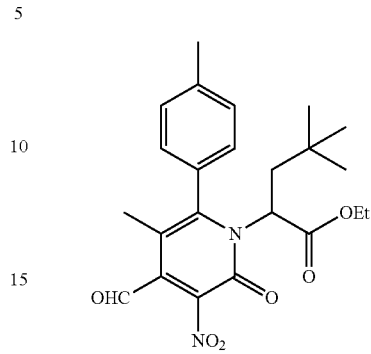

To a solution of Ethyl 2-(4-(hydroxymethyl)-5-methyl-3-nitro-2-oxo-6-(p-tolyl)pyridin-1(2H)-yl)-4,4-dimethylpentanoate (33 mg, 0.08 mmol) in DCM (5 mL) was added DMP (49 mg, 0.12 mmol). After 1 h, the reaction mixture was quenched with NaHCO$_3$(aq.) and extracted with DCM (20 mL×3). The combined organic layers was washed with brine, dried over Na$_2$SO$_4$, filtered and concentrated under reduced pressure to give the crude product which was purified by column chromatography (silica gel, DCM) to afford the title compound as a yellow solid (27 mg, 82% yield). LC-MS (ESI): m/z (M+1)=429.5.

Step 4: 1-(1-Ethoxy-4,4-dimethyl-1-oxopentan-2-yl)-5-methyl-3-nitro-2-oxo-6-(p-tolyl)-1,2-dihydropyridine-4-carboxylic acid

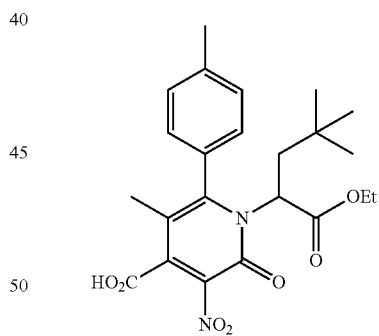

To a solution of Ethyl 2-(4-formyl-5-methyl-3-nitro-2-oxo-6-(p-tolyl)pyridin-1(2H)-yl)-4,4-dimethyl pentanoate (27 mg, 0.06 mmol) in THF (1 mL), t-BuOH (1 mL) and isobutylene (1 ml) in a sealed tube was added a solution of NaH$_2$PO$_4$ (59 mg, 0.38 mmol) and NaClO$_2$ (46 mg, 0.50 mmol) in H$_2$O (1 mL). After 12 h, the reaction mixture was acidified with 1 N HCl and extracted with EtOAc (20 mL×3). The combined organic layers was washed with brine, dried over Na$_2$SO$_4$, filtered and concentrated under reduced pressure to give the title compound as a yellow solid (30 mg, 99% yield) which was used in next step without further purification. LC-MS (ESI): m/z (M+1)=445.5

Step 6: Ethyl 4,4-dimethyl-2-(5-methyl-4-(((1s,4s)-4-methylcyclohexyl)carbamoyl)-3-nitro-2-oxo-6-(p-tolyl)pyridin-1(2H)-yl)pentanoate

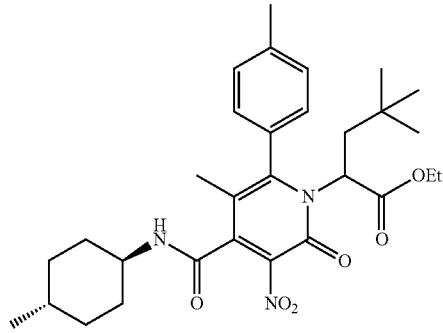 [SMILES: CCOC(=O)C(CC(C)(C)C)n1c(-c2ccc(C)cc2)c(C)c(C(=O)N[C@H]2CC[C@H](C)CC2)c([N+](=O)[O-])c1=O]

A solution of 1-(1-ethoxy-4,4-dimethyl-1-oxopentan-2-yl)-5-methyl-3-nitro-2-oxo-6-(p-toly)-1,2-dihydropyridine-4-carboxylic acid (30 mg, 0.067 mmol) in DMF (3 mL) was treated with DIPEA (35 mg, 0.27 mmol), HBTU (52 mg, 0.13 mmol) and trans-4-methyl cyclohexyl amine (15 mg, 0.14 mmol). After 30 min, the reaction mixture was diluted with water and extracted with EtOAc (20 ml×3). The combined organic layers was washed with brine, dried over $Na_2SO_4$, filtered and concentrated under reduced pressure to give the crude product which was purified by column chromatography (silica gel, PE:EA=2:1) to afford the title compound as a yellow oil (18 mg, 50%). LC-MS (ESI): m/z (M+1)=540.8.

Step 7: Ethyl 2-(3-amino-5-methyl-4-(((1s,4s)-4-methylcyclohexyl)carbamoyl)-2-oxo-6-(p-tolyl)pyridin-1(2H)-yl-4,4-dimethylpentanoate

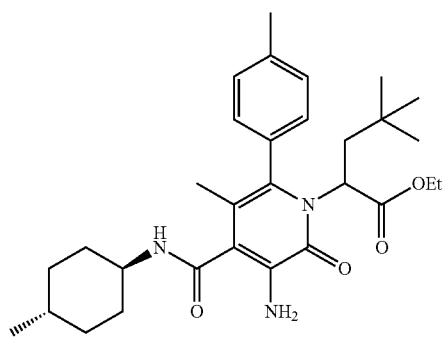 [SMILES: CCOC(=O)C(CC(C)(C)C)n1c(-c2ccc(C)cc2)c(C)c(C(=O)N[C@H]2CC[C@H](C)CC2)c(N)c1=O]

A mixture of Ethyl 4,4-dimethyl-2-(5-methyl-4-(((1s,4s)-4-methylcyclohexyl)carbamoyl)-3-nitro-2-oxo-6-(p-tolyl)pyridin-1(2H)-yl)pentanoate (18 mg, 0.03 mmol) and Pd/C (10 mg) in EtOAc (5 mL) was purged with $H_2$ three times. After 12 h, the reaction mixture was filtered through Celite pad and the filtrate was concentrated under reduced pressure to afford the title compound as a yellow solid (10 mg, 65% yield). LC-MS (ESI): m/z (M+1)=510.6.

Step 8: Ethyl 4,4-dimethyl-2-(5-methyl-4-(((1s,4s)-4-methylcyclohexyl)carbamoyl)-3-(methylsulfonamido)-2-oxo-6-(p-tolyl)pyridin-1(2H)-yl)pentanoate

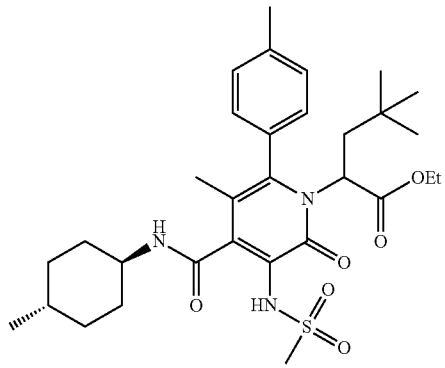 [SMILES: CCOC(=O)C(CC(C)(C)C)n1c(-c2ccc(C)cc2)c(C)c(C(=O)N[C@H]2CC[C@H](C)CC2)c(NS(C)(=O)=O)c1=O]

To a solution of Ethyl 2-(3-amino-5-methyl-4-(((1s,4s)-4-methylcyclohexyl)carbamoyl)-2-oxo-6-(p-tolyl)pyridin-1(2H)-yl)-4,4-dimethylpentanoate (19 mg, 0.037 mmol) and DMAP (1 mg, 0.008 mmol) in pyridine (2 mL) was added MsCl (0.03 mL, 0.37 mmol). After 2 h, the reaction mixture was diluted with water and extracted with EtOAc (20 ml×2). The combined organic layers were washed with brine, dried over $Na_2SO_4$, filtered and concentrated under reduced pressure to give the crude product which was purified by column chromatography (silica gel, PE:EA=2:1) to afford the title compound as a yellow oil (5 mg, 23% yield). LC-MS (ESI): m/z (M+1)=588.7.

Step 9: 4,4-Dimethyl-2-(5-methyl-4-(((1s,4s)-4-methylcyclohexyl)carbamoyl)-3-(methylsulfonamido)-2-oxo-6-(p-tolyl)pyridin-1(2H)-yl)pentanoic acid

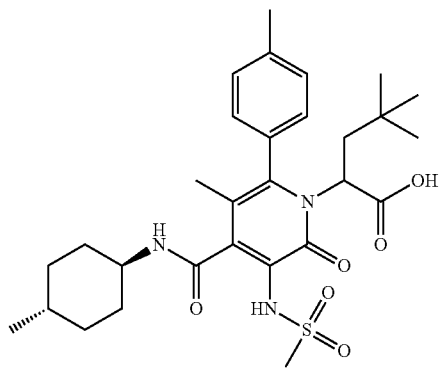 [SMILES: Cc1ccc(-c2c(C)c(C(=O)N[C@H]3CC[C@H](C)CC3)c(NS(C)(=O)=O)c(=O)n2C(CC(C)(C)C)C(=O)O)cc1]

To a solution of Ethyl 4,4-dimethyl-2-(5-methyl-4-(((1s,4s)-4-methylcyclohexyl)carbamoyl)-3-(methylsulfonamido)-2-oxo-6-(p-tolyl)pyridin-1(2H)-yl)pentanoate (5 mg, 0.008 mmol) in MeOH (2 mL) was added 1 N NaOH (0.2 mL) and heated to reflux. After 12 h, the reaction mixture was cooled to ambient temperature, acidified with 1 N HCl (0.2 mL) (pH=6~7) and concentrated under reduced pressure to give the crude product which was purified by reverse phase HPLC ($C_{18}$ 10~100% $CH_3CN$ in $H_2O$ with 0.1% formic acid) to afford the title compound as a white powder (3 mg, 67% yield). ¹H NMR (400 MHz, DMSO) δ 8.33 (s, 1H), 7.87 (d, J=7.2 Hz, 1H), 7.48-7.34 (m, 3H), 7.26 (d, J=7.6 Hz, 1H), 4.19 (s, 1H), 3.65-3.61 (m, 1H), 3.14 (s, 3H), 2.39 (s, 3H), 2.31-2.26 (m, 1H), 1.93-1.80 (m, 3H), 1.75-1.56 (m, 5H), 1.32-1.20 (m, 3H), 1.03-0.94 (m, 2H), 0.87 (d, J=6.4 Hz, 3H), 0.57 (s, 9H). LC-MS (ESI): m/z (M+1)=560.6.

Scheme 6

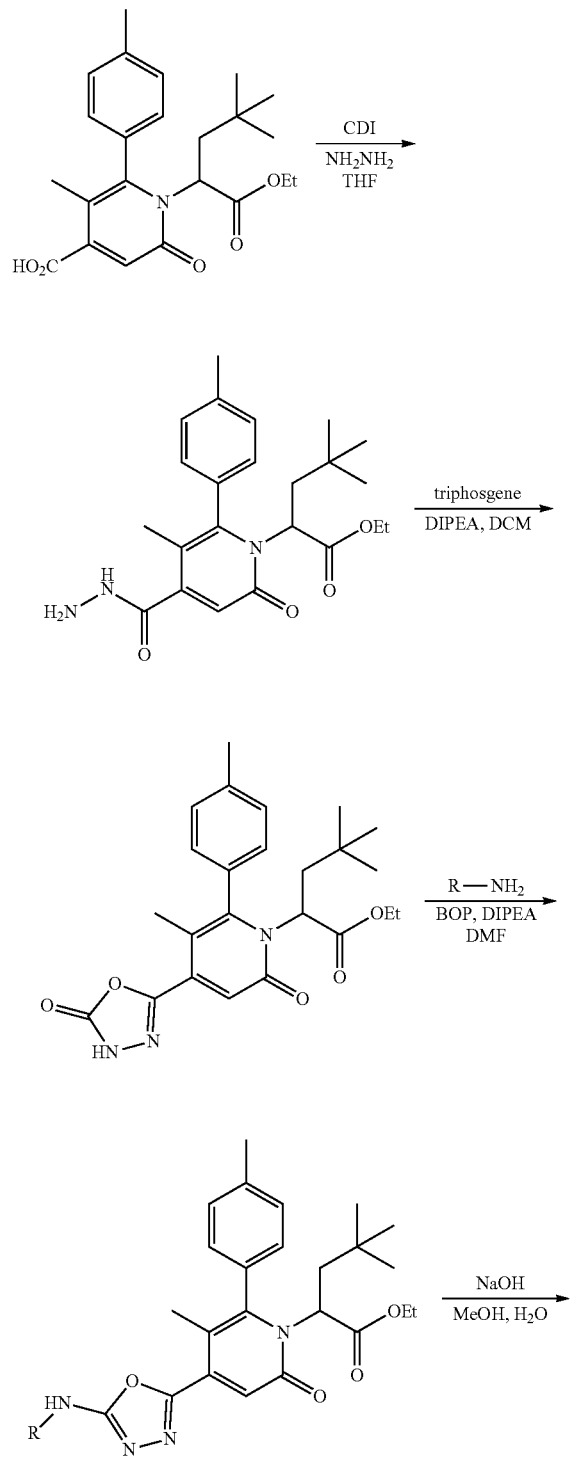

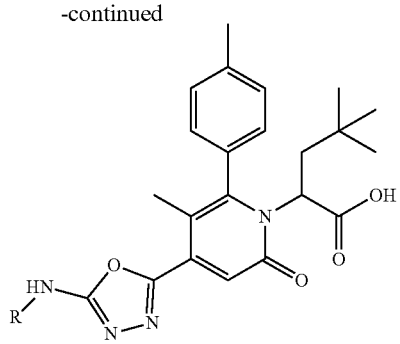

Example 6: 4,4-Dimethyl-2-(5-methyl-4-(5-(((1r,4r)-4-methylcyclohexyl)amino)-1,3,4-oxadiazol-2-yl)-2-oxo-6-(p-tolyl)pyridin-1(2H)-yl)pentanoic acid

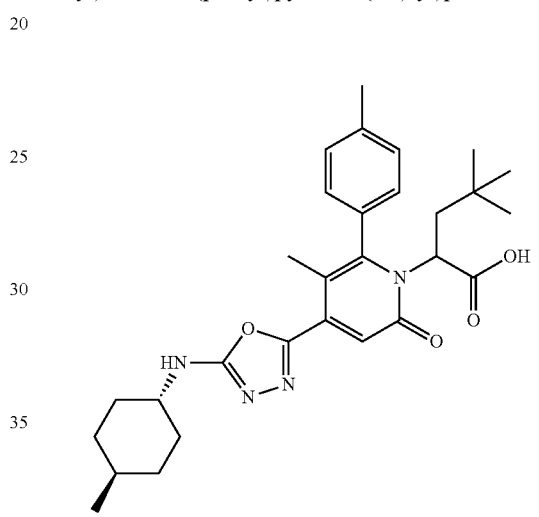

Step 1: Ethyl 2-(4-(hydrazinecarbonyl)-5-methyl-2-oxo-6-(p-tolyl)pyridin-1(2H)-yl)-4,4-dimethylpentanoate

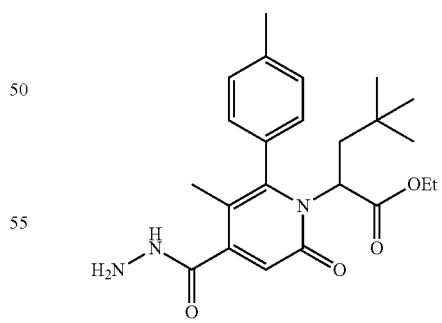

To a solution of 1-(1-ethoxy-4,4-dimethyl-1-oxopentan-2-yl)-5-methyl-2-oxo-6-p-tolyl-1,2-dihydropyridine-4-carboxylic acid (66 mg, 0.165 mmol) in THF (3 mL) was added CDI (107 mg, 0.66 mmol). After 30 min, hydrazine (0.1 mL, 1.65 mmol) was added and stirred for 1 h. The reaction mixture was concentrated under reduced pressure to give the crude product which was purified by column chromatography (silica gel, DCM:MeOH=10:1) to afford the title compound as a colorless oil (44 mg, 64% yield). LC-MS (ESI): m/z (M+1)=414.4.

Step 2: Ethyl 4,4-dimethyl-2-(5-methyl-2-oxo-4-(5-oxo-4,5-dihydro-1,3,4-oxadiazol-2-yl)-6-(p-tolyl)pyridin-1(2H)-yl)pentanoate

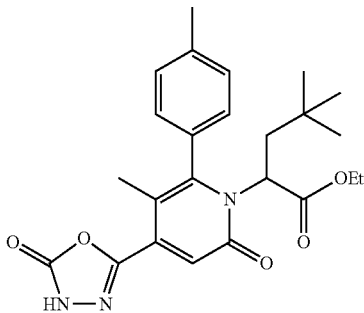 [SMILES: CCOC(=O)C(CC(C)(C)C)n1c(-c2ccc(C)cc2)c(C)c(-c2n[nH]c(=O)o2)cc1=O]

To a solution of Ethyl 2-(4-(hydrazinecarbonyl)-5-methyl-2-oxo-6-(p-tolyl)pyridin-1(2H)-yl)-4,4-dimethylpentanoate (44 mg, 0.11 mmol) and DIPEA (0.04 mL, 0.22 mmol) in DCM (2 mL) was added triphosgene (13 mg, 0.04 mmol). After 30 min, the reaction mixture was quenched with water and extracted with DCM (20 ml×2). The combined organic layers were washed with brine, dried over Na$_2$SO$_4$, filtered and concentrated under reduced pressure to give the crude product which was purified by column chromatography (silica gel, PE:EA=1:1) to afford the title compound as a yellow oil (46 mg, 100% yield). LC-MS (ESI): m/z (M+1)=440.4.

Step 3: Ethyl 4,4-dimethyl-2-(5-methyl-4-(5-(((1r,4r)-4-methylcyclohexyl)amino)-1,3,4-oxadiazol-2-yl)-2-oxo-6-(p-tolyl)pyridin-1(2H)-yl)pentanoate

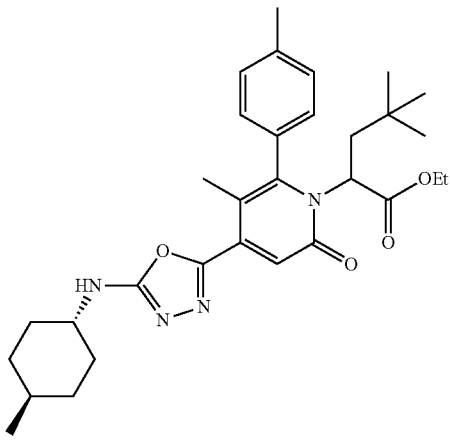 [SMILES: CCOC(=O)C(CC(C)(C)C)n1c(-c2ccc(C)cc2)c(C)c(-c2nnc(N[C@H]3CC[C@H](C)CC3)o2)cc1=O]

A mixture of Ethyl 4,4-dimethyl-2-(5-methyl-2-oxo-4-(5-oxo-4,5-dihydro-1,3,4-oxadiazol-2-yl)-6-(p-tolyl)pyridin-1(2H)-yl)pentanoate (25 mg, 0.06 mmol), (1r,4r)-4-methylcyclohexanamine (0.015 mL, 0.11 mmol), BOP (28 mg, 0.063 mmol) and DIPEA (0.02 mL, 0.11 mmol) in DMF (2 mL) was stirred at ambient temperature for 12 h. The reaction mixture was diluted with water and extracted with EtOAc (20 ml×2). The combined organic layers were washed with brine, dried over Na$_2$SO$_4$, filtered and concentrated under reduced pressure to give the crude product which was purified by column chromatography (silica gel, PE:EA=1:1) to afford the title compound as a yellow oil (20 mg, 66% yield). LC-MS (ESI): m/z (M+1)=535.6.

Step 4: 4,4-Dimethyl-2-(5-methyl-4-(5-(((1r,4r)-4-methylcyclohexyl)amino)-1,3,4-oxadiazol-2-yl)-2-oxo-6-(p-tolyl)pyridin-1(2H)-yl)pentanoic acid

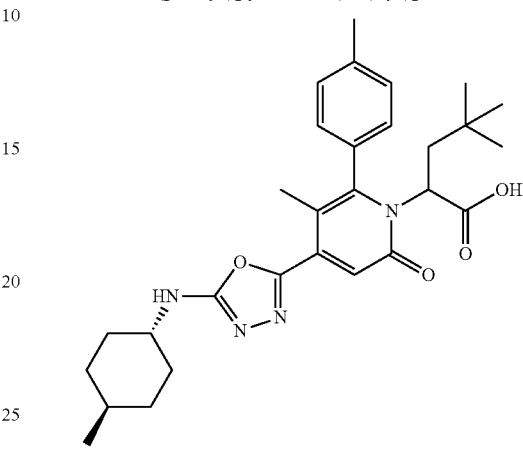

To a solution of Ethyl 4,4-dimethyl-2-(5-methyl-4-(5-(((1r,4r)-4-methylcyclohexyl)amino)-1,3,4-oxadiazol-2-yl)-2-oxo-6-(p-toly)pyridin-1(2H)-yl)pentanoate (20 mg, 0.037 mmol) in MeOH (2 mL) was added 1 N NaOH (0.4 mL) and heated to reflux. After 12 h, the reaction mixture was cooled to ambient temperature, acidified with 1 N HCl (0.4 mL) (pH=6~7) and concentrated under reduced pressure to give the crude product which was purified by reverse phase HPLC (C$_{18}$ 60~100% CH$_3$CN in H$_2$O with 0.1% formic acid) to afford the title compound as a white powder (8 mg, 42% yield). $^1$H NMR (400 MHz, DMSO) δ 12.86 (s, 1H), 7.96 (d, J=7.5 Hz, 1H), 7.45-7.30 (m, 4H), 6.75 (s, 1H), 4.28 (s, 1H), 3.39-3.36 (m, 1H), 2.41 (s, 3H), 2.26-2.22 (m, 1H), 2.06-1.93 (m, 5H), 1.92-1.87 (m, 1H), 1.75-1.68 (m, 2H), 1.37-1.27 (m, 3H), 1.08-1.01 (m, 2H), 0.89 (d, J=6.5 Hz, 3H), 0.59 (s, 9H). LC-MS (ESI): m/z (M+1)=507.6.

The following compounds were prepared in a manner similar to the procedures described above for examples 1-6.

Example 7: 2-(4-(cyclohexylcarbamoyl)-5-methyl-2-oxo-6-p-tolylpyridin-1(2H)-yl)-4,4-dimethylpentanoic acid

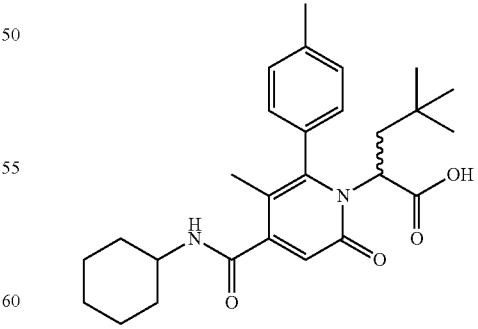

$^1$H NMR (400 MHz, DMSO) δ=12.78 (br, 1H), 8.47 (d, J=8.0 Hz, 1H), 7.36 (m, 4H), 6.27 (s, 1H), 4.22 (s, 1H), 3.71-3.63 (m, 1H), 2.39 (s, 3H), 2.32-2.26 (m, 1H), 1.84-1.64 (m, 7H), 1.60-1.54 (m, 1H), 1.34-1.06 (m, 6H), 0.58 (s, 9H). LC-MS (ESI): m/z (M+1)=453.6

Example 8: 2-(4-(cyclohexylmethylcarbamoyl)-5-methyl-2-oxo-6-p-tolylpyridin-1(2H)-yl)-4,4-dimethylpentanoic acid

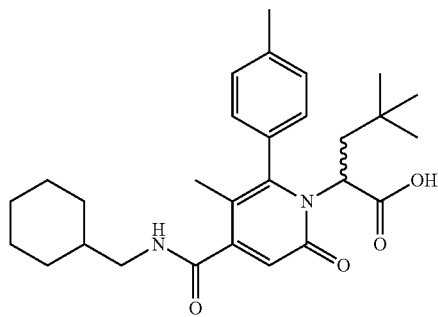 [SMILES: Cc1ccc(-c2c(C)c(C(=O)NCC3CCCCC3)cc(=O)n2C(CC(C)(C)C)C(=O)O)cc1]

¹H NMR (400 MHz, DMSO) δ=12.92 (br, 1H), 8.57 (t, J=5.9 Hz, 1H), 7.42-7.28 (m, 4H), 6.29 (s, 1H), 4.23 (s, 1H), 3.08-3.01 (m, 2H), 2.39 (s, 3H), 2.32-2.24 (m, 1H), 1.90-1.80 (m, 1H), 1.74-1.58 (m, 8H), 1.52-1.44 (m, 1H), 1.24-1.13 (m, 3H), 0.96-0.86 (m, 2H), 0.59 (s, 9H). LC-MS (ESI): m/z (M+1)=467.6

Example 9: 2-(4-(benzylcarbamoyl)-5-methyl-2-oxo-6-p-tolylpyridin-1(2H)-yl)-4,4-dimethylpentanoic acid

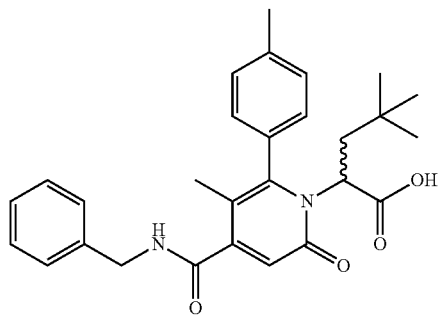 [SMILES: Cc1ccc(-c2c(C)c(C(=O)NCc3ccccc3)cc(=O)n2C(CC(C)(C)C)C(=O)O)cc1]

¹H NMR (400 MHz, DMSO) δ 12.86 (br, 1H), 9.15 (t, J=5.8 Hz, 1H), 7.67-6.96 (m, 9H), 6.38 (s, 1H), 4.41 (d, J=4.7 Hz, 2H), 4.25 (s, 1H), 2.39 (s, 3H), 2.32-2.22 (m, 1H), 1.92-1.78 (m, 1H), 1.67 (s, 3H), 0.59 (s, 9H). LC-MS (ESI): m/z (M+1)=461.3

Example 10: 2-(3-(cyclohexylmethylsulfonamido)-5-methyl-2-oxo-6-(p-tolyl)pyridin-1(2H)-yl)-4,4-dimethylpentanoic acid

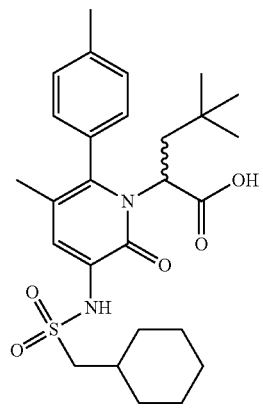 [SMILES: Cc1ccc(-c2c(C)cc(NS(=O)(=O)CC3CCCCC3)c(=O)n2C(CC(C)(C)C)C(=O)O)cc1]

1H NMR (400 MHz, DMSO) δ 12.93 (br, 1H), 8.82 (s, 1H), 7.46-7.25 (m, 5H), 4.31 (s, 1H), 3.05 (d, J=6.1 Hz, 2H), 2.39 (s, 3H), 2.25-2.19 (m, 1H), 2.04-1.97 (m, 1H), 1.92-1.78 (m, 5H), 1.68-1.56 (m, 3H), 1.24-0.99 (m, 5H), 0.56 (s, 9H). LC-MS (ESI): m/z (M+1)=503.3

Example 11: 2-(6-(8-fluoro-5-methylchroman-6-yl)-5-methyl-4-(((1s,4s)-4-methylcyclohexyl)carbamoyl)-2-oxopyridin-1(2H)-yl)-4,4-dimethylpentanoic acid

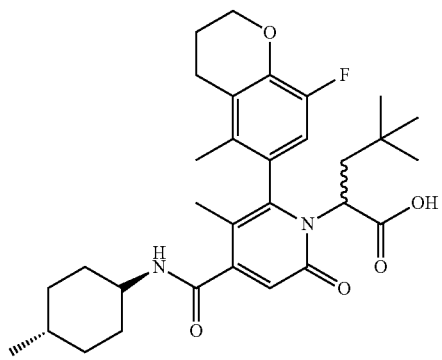

1H NMR (400 MHz, DMSO) δ 8.45 (d, J=8.1 Hz, 1H), 7.03-6.84 (m, 1H), 6.23 (s, 1H), 4.23-4.15 (m, 3H), 3.61-3.55 (m, 1H), 2.72-2.56 (m, 2H), 2.42-2.32 (m, 1H), 2.05-1.88 (m, 5H), 1.85-1.75 (m, 2H), 1.71-1.62 (m, 2H), 1.55 (d, J=24.2 Hz, 3H), 1.33-1.16 (m, 4H), 1.03-0.91 (m, 2H), 0.85 (d, J=6.5 Hz, 3H), 0.61 (d, J=33.7 Hz, 9H). LC-MS (ESI): m/z (M+1)=541.9

Biological Examples

Anti-HIV Activity

MT4 Assay

Antiviral HIV activity and cytotoxicity values for compounds of the invention from Table 1 were measured in parallel in the HTLV-1 transformed cell line MT-4 based on the method previously described (Hazen et al., 2007, In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV (Hazen et al., "In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV", *Antimicrob. Agents Chemother.* 2007, 51: 3147-3154; and Pauwels et al., "Sensitive and rapid assay on MT-4 cells for the detection of antiviral compounds against the AIDS virus", *J. of Virological Methods* 1987, 16: 171-185).

Luciferase activity was measured 96 hours later by adding a cell titer glo (Promega, Madison, Wis.). Percent inhibition of cell protection data was plotted relative to no compound control. Under the same condition, cytotoxicity of the compounds was determined using cell titer Glo™ (Promega, Madison, Wis.). IC$_{50}$s were determined from a 10 point dose response curve using 3-4-fold serial dilution for each compound, which spans a concentration range >1000 fold.

These values are plotted against the molar compound concentrations using the standard four parameter logistic equation:

$$y=((V\max * x\hat{\,}n)/(K\hat{\,}n+x\hat{\,}n))+Y2$$

where:
Y2=minimum y n=slope factor
Vmax=maximum y x=compound concentration [M]
K=$EC_{50}$ When tested in the MT4 assay compounds were found to have $IC_{50}$ values listed in Table 2.

TABLE 2

| Example | HIV MT4 Assay $IC_{50}$ (uM) |
|---|---|
| 1 | 0.35 |
| 2 | 1.09 |
| 3 | 0.31 |
| 4 | 33 |
| 5 | |
| 6 | 5.6 |
| 7 | 0.43 |
| 8 | 0.84 |
| 9 | 3.29 |
| 10 | 1.56 |
| 11 | |

What is claimed is:

1. A compound of Formula I:

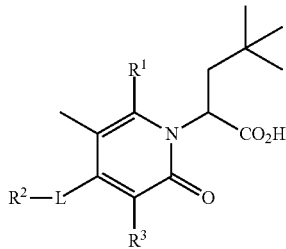

Formula I wherein:
R$^1$ is phenyl optionally substituted by one to four substituents selected from $C_{1-3}$alkyl, halogen, or —CH$_2$CH$_2$CH$_2$O— wherein this group is bonded to adjacent carbon atoms on the phenyl to form a ring;

L is a bond, $C_{1-3}$alkylene, —SO$_2$—, —SO$_2$CH$_2$—, —NHSO$_2$—, —NHSO$_2$CH$_2$—, —C(O)—, —C(O)NH—, —C(O)NHCH$_2$—, —C(O)OCH$_2$—, —C(O)C(O)—, —CH$_2$C(O)—, $C_{3-7}$heteroaryl, or —$C_{3-7}$heteroarylNH—, wherein each heteroaryl comprises one to three heteroatoms selected from S, N, and O;

R$^2$ is H, cyclohexyl, or phenyl wherein said cyclohexyl and phenyl are optionally substituted by one to three substituents selected from $C_{1-3}$alkyl and halogen R$^3$ is H or —NHSO$_2$R$^4$ wherein R$^4$ is $C_{1-8}$alkyl and wherein said alkyl can include cycloalkyl portions.

2. A compound according to claim 1 wherein R$^1$ is phenyl optionally substituted by a methyl group.

3. A compound according to claim 1 wherein L is a bond, -oxadiazolyl-NH—, —C(O)NH—, or —C(O)NHCH$_2$—.

4. A compound according to claim 1 wherein R$^2$ is H, cyclohexyl, or phenyl wherein said cyclohexyl and phenyl are optionally substituted by 1 or 2 methyl groups.

5. A compound according to claim 1 wherein R$^3$ is H, —NHSO$_2$CH$_3$, or —NHSO$_2$CH$_2$cyclohexyl.

6. A compound according to claim 1 wherein the stereochemistry on the carbon to which the t-butyl group is bound is as depicted below.

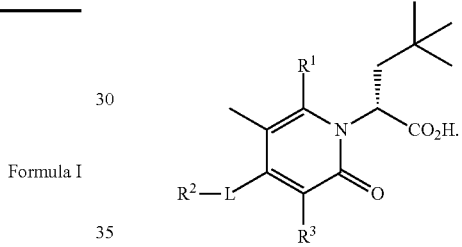

7. A pharmaceutically acceptable salt of a compound according to claim 1.

8. A pharmaceutical composition comprising a compound according to claim 1 or a pharmaceutically acceptable salt thereof.

9. A method for treating a viral infection in a patient mediated at least in part by a virus in the retrovirus family of viruses, comprising administering to said patient a composition according to claim 8.

10. The method of claim 9 wherein said viral infection is mediated by the HIV virus.

* * * * *